(12) United States Patent
Boldingh et al.

(10) Patent No.: US 7,626,064 B1
(45) Date of Patent: *Dec. 1, 2009

(54) TRANSALKYLATION PROCESS

(75) Inventors: Edwin P. Boldingh, Arlington Heights, IL (US); Michael G. Gatter, Elk Grove Village, IL (US); Susan C. Koster, Carpentersville, IL (US); David S. Lafyatis, Schaumburg, IL (US); Terrence E. Deak, Chicago, IL (US); Eric J. Baker, Chicago, IL (US); Robert W. Broach, Deerfield, IL (US); Deng-Yang Jan, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/146,831

(22) Filed: Jun. 26, 2008

(51) Int. Cl.
*C07C 6/12* (2006.01)
(52) U.S. Cl. ..................................................... 585/475
(58) Field of Classification Search .................. 585/475
See application file for complete search history.

(56) References Cited

U.S. PATENT DOCUMENTS

| | | | |
|---|---|---|---|
| 3,562,345 A | 2/1971 | Mitsche | 260/672 |
| 3,912,659 A | 10/1975 | Brandenburg et al. | 252/455 Z |
| 5,804,059 A | 9/1998 | Wu et al. | 208/135 |
| 5,847,256 A | 12/1998 | Ichioka et al. | 585/470 |
| 6,040,490 A | 3/2000 | Ichioka et al. | 585/475 |
| 6,060,417 A | 5/2000 | Kato et al. | 502/66 |
| 6,137,020 A | 10/2000 | Butler et al. | 585/446 |
| 6,486,372 B1 | 11/2002 | Merlen et al. | 585/467 |
| 6,858,129 B2 | 2/2005 | Mohr et al. | 208/120.01 |
| 6,984,764 B1 | 1/2006 | Roth et al. | 585/323 |
| 7,148,391 B1 | 12/2006 | Buchanan et al. | 585/475 |
| 7,202,189 B2 | 4/2007 | Negiz et al. | 502/74 |
| 7,220,885 B2 | 5/2007 | Boldingh et al. | 585/475 |
| 2003/0181774 A1 | 9/2003 | Kong et al. | 585/475 |

OTHER PUBLICATIONS

U.S. Appl. No. 12/146,847, filed Jun. 26, 2008, Moscoso et al.
U.S. Appl. No. 12/146,865, filed Jun. 26, 2008, Lafyatis et al.
Selvam, T. et al., "Selective isopropylation of biphenyl to 4,4'-DIPB over mordenite (MOR) type zeolite obtained from a layered sodium silicate magadiite" *Catalysis Letters* vol. 94, Nos. 1-2, Apr. 2004, 2004 Plenum Publishing Corporation, pp. 17-24.
Kong, D., et al., "Technological advances in conversion of heavy aromatics to light aromatics" (9 pages).
Lee, H.S., et al., "Toluene Disproportionation Over Metal Loaded Mordenites Catalytic Activity, Selectivity and Aging" *Korean J. of Chem. Eng.*, &(4) (1990) pp. 243-249.
Serra, J.M., et al., "Optimizing the conversion of heavy reformate streams into xylenes with zeolite catalysts by using knowledge base high-throughput experimentation techniques" *Journal of Catalysis* 232 (2005) pp. 342-354.

*Primary Examiner*—Thuan Dinh Dang
(74) *Attorney, Agent, or Firm*—David J. Piasecki

(57) ABSTRACT

This invention embodies a catalyst and a process for transalkylation of $C_7$, $C_9$, and $C_{10}$ aromatics to obtain a high yield of xylenes. The catalyst comprises a novel UZM-14 catalytic material comprising globular aggregates of crystallites having a MOR framework type with a mean crystallite length parallel to the direction of the 12-ring channels of about 60 nm or less and a mesopore volume of at least about 0.10 cc/gram. The UZM-14 catalyst is particularly active and stable in a transalkylation process.

11 Claims, 1 Drawing Sheet

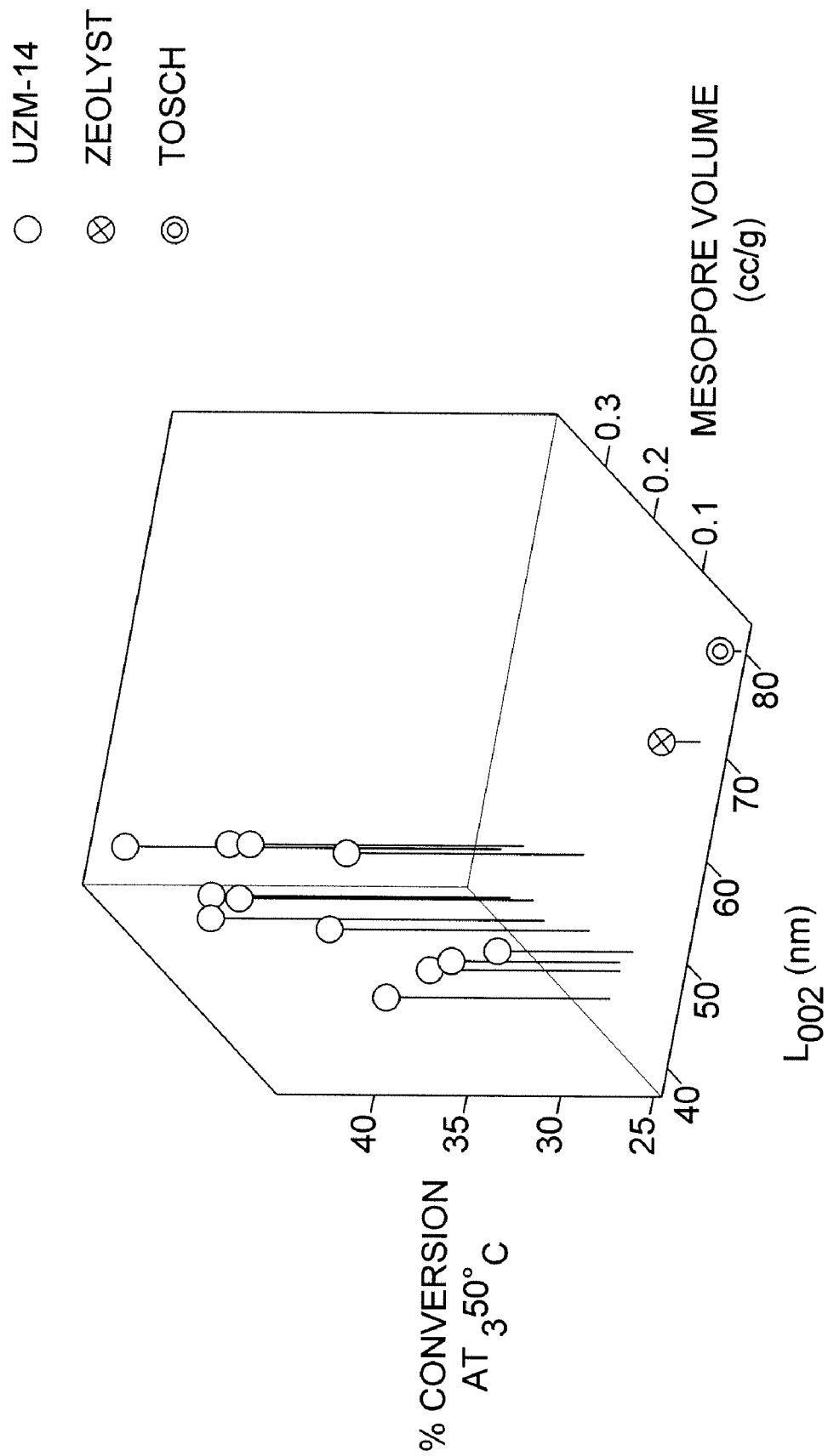

TRANSALKYLATION PROCESS

FIELD OF THE INVENTION

The present invention relates to a catalyst and process for the conversion of aromatic hydrocarbons, and more specifically for the transalkylation of aromatic hydrocarbons to obtain xylenes.

BACKGROUND OF THE INVENTION

The xylene isomers are produced in large volumes from petroleum as feedstocks for a variety of important industrial chemicals. The most important of the xylene isomers is paraxylene, the principal feedstock for polyester which continues to enjoy a high growth rate from a large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Toluene commonly is dealkylated to produce benzene or disproportionated to yield benzene and $C_8$ aromatics from which the individual xylene isomers are recovered. More recently, processes have been commercialized to transalkylate heavier aromatics along with toluene selectively to increase the yield xylenes from aromatics complexes.

The art teaches a variety of catalysts for the transalkylation of aromatic hydrocarbons. A wide range of zeolites, including mordenite, have been disclosed as effective transalkylation catalysts. Shaped catalysts, multiple zeolites, metal modifiers, and treatments such as steam calcination have been described as increasing the effectiveness of the catalysts. There is a need to improve catalyst stability and the conversion of heavy material.

SUMMARY OF THE INVENTION

In accordance with the present invention there is provided a novel modified form of mordenite having adsorption properties and catalytic activity significantly different from those possessed by any of the known prior art forms of mordenite.

A principal object of the present invention is to provide a process for the transalkylation of alkylaromatic hydrocarbons. More specifically, the process of the present invention is directed to converting aromatic hydrocarbons with improved yields of desired xylene isomers over a UZM-14 catalyst demonstrating improved activity in transalkylating toluene with $C_9$-$C_{11}$+ aromatics.

Accordingly, a broad embodiment of the present invention is a process for transalkylation of a feedstream comprising one or more of $C_7$, $C_9$, $C_{10}$ and $C_{11}$+ aromatics to obtain a transalkylation product stream having an increased concentration of $C_8$ aromatics relative to that of the feedstream, comprising contacting the feedstream at transalkylation conditions with a catalyst comprising a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less.

A more specific embodiment is a process for transalkylation of a feedstream comprising $C_7$, $C_9$, $C_{10}$ and $C_{11}$+ aromatics to obtain a product stream having an increased concentration of $C_8$ aromatics relative to that of the feedstream, comprising contacting the feedstream at transalkylation conditions with a catalyst comprising a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less, a binder selected from one or more of alumina, silica and silica-alumina, and a metal component comprising one component comprising one or more elements selected from groups VIB(6), VIIB(7), VIII(8-10) and IVA (14) of the Periodic Table.

A yet more specific embodiment is a process for transalkylation of a feedstream comprising $C_7$, $C_9$, $C_{10}$ and $C_{11}$+ aromatics to obtain a product stream having an increased concentration of $C_8$ aromatics relative to that of the feedstream, comprising contacting the feedstream at transalkylation conditions with a catalyst suitable for the conversion of aromatic hydrocarbons comprising a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less, an additional zeolitic component selected from one or more of MFI, MEL, EUO, FER, MFS, MTT, MTW, TON, MOR and FAU, a binder comprising one or more of alumina, silica and silica-alumina, and a metal component comprising one or more elements selected from groups VIB(6), VIIB(7), VIII(8-10) and IVA(14) of the Periodic Table.

These, as well as other objects and embodiments will become evident from the following detailed description of the invention.

BRIEF DESCRIPTION OF THE DRAWING

The FIGURE is a three-dimensional comparison of mean crystallite length parallel to the direction of the 12-ring channels, mesopore volume and conversion obtained with several samples.

DETAILED DESCRIPTION OF THE INVENTION

The feedstream to the present process comprises alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, diisopropylbenzenes, and mixtures thereof.

The aromatics-rich feed stream to a transalkylation or disproportionation process may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the complex in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of nonaromatics in the product. The reformate also advantageously is subjected to olefin saturation to remove potential product contaminants and materials that could polymerize to heavy nonconvertibles in a transalkylation process. Such processing steps are described in U.S. Pat. No. 6,740,788 B1, incorporated herein by reference thereto.

The feed stream to a transalkylation or disproportionation process can be a substantially pure alkylaromatic hydrocarbon of from about 6 to about 15 carbon atoms, a mixture of such alkylaromatic hydrocarbons, or a hydrocarbon fraction rich in said alkylaromatics. The feed stream comprises alkylaromatic hydrocarbons of the general formula $C_6H_{(6-n)}R_n$, where n is an integer from 1 to 5 and R is one or more of $CH_3$, $C_2H_5$, $C_3H_7$, $C_4H_9$, or $C_5H_{11}$ in any combination. The feed stream also may comprise benzene and aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethylbenzenes, diethyl-benzenes, triethylbenzenes, propylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of nonaromatics such as pentanes, hexanes, heptanes and heavier paraffins along with paraffins along with methylcyclopentane, cyclohexane and heavier naphthenes; pentanes and lighter paraffins generally will have been removed before processing in the aromatics complex. The combined transalkylation feed preferably contains no more than about 10 wt-% nonaromatics; olefins preferably are restricted to a Bromine Index of no more than about 1000, and preferably no more than about 500.

A preferred component of the feedstock is a heavy-aromatics stream comprising C9 aromatics, thereby effecting transalkylation of toluene and C9 aromatics to yield additional xylenes. Benzene may also be transalkylated to yield additional toluene. Indane may be present in the heavy-aromatics stream although it is not a desirable component to effect high yields of C8 aromatics product. C10+ aromatics also may be present, preferably in an amount of 30% or less of the feed. The heavy-aromatics stream preferably comprises at least about 90 mass-% aromatics, and may be derived from the same or different known refinery and petrochemical processes as the benzene and toluene feedstock and/or may be recycled from the separation of the product from transalkylation.

The feedstock is preferably transalkylated in the vapor phase and in the presence of hydrogen. If transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having an increased xylene content and also comprises toluene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. Passage of the combined feed through the reaction zone effects the production of an effluent stream comprising unconverted feed and product hydrocarbons. This effluent is normally cooled by indirect heat exchange against the the stream entering the reaction zone and then further cooled through the use of air or cooling water. The effluent may be passed into a stripping column in which substantially all C5 and lighter hydrocarbons present in the effluent are concentrated into an overhead stream and removed from the process. An aromatics-rich stream is recovered as net stripper bottoms which is referred to herein as the transalkylation effluent.

The transalkylation or disproportionation reaction can be effected in contact with the catalytic composite of this invention in any conventional or otherwise convenient manner and may comprise a batch or continuous type of operation, with a continuous operation being preferred. The catalyst usefully is disposed as a fixed bed in a reaction zone of a vertical tubular reactor with the alkylaromatic feed stock charged through the bed in an upflow or downflow manner. Conditions employed in the transalkylation zone normally include a temperature of from about 200° to about 540° C., preferably between about 200° to about 480° C. The transalkylation zone is operated at moderately elevated pressures broadly ranging from about 100 kPa to about 6 Mpa absolute. The transalkylation reaction can be effected over a wide range of space velocities, i.e., volume of charge per volume of catalyst per hour, liquid hourly space velocity generally is in the range of from about 0.1 to about 20 hr-1. The catalyst is particularly noteworthy for its relatively high stability at a high activity level.

The transalkylation effluent is separated into a light recycle stream, a mixed C8 aromatics product and a heavy-aromatics stream. The mixed C8 aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the C9 and heavier aromatics and may be partially or totally recycled to the transalkylation reaction zone.

The UZM-14 of the present invention is a novel aluminosilicate zeolite with unique adsorption properties and catalytic activity, having a MOR framework type as described in Atlas of Zeolite Framework Types, 6th Revised Edition, C. H. Baerlocher, L. B. McCusker, and D. H. Olson, editors, Elsevier (2007), pp. 218-219. The MOR structure comprises four- and five-membered rings of the $SiO_4$ and $AlO_4$ tetrahedra so arranged that the crystal lattice comprises 12-ring channels running parallel along the crystal axis to give a tubular configuration. The zeolite usually is characterized by a silica-alumina mole ratio of from about 10 to about 50. The invention is based on the discovery that specific crystal characteristics allow increased accessibility to the internal micropore volume for improved activity and selectivity in transalkylating aromatics.

The UZM-14 aggregate material of the invention features one or more of the following distinctive characteristics:

(1) globular aggregates have a mesopore volume of at least about 0.10 cc/gram, and preferably at least about 0.13 cc/gram;

(2) the UZM-14 crystallites have at least about $1 \times 10^{19}$ 12-ring channels/gram of UZM-14 material;

(3) the mean crystallite length parallel to the direction of the 12-ring channels is about 60 nm or less and preferably about 50 nm or less;

(4) The Si/Al2 ratio of the UZM-14 aggregate material generally is between about 8 and about 50, and preferably no more than about 30.

The UZM-14 of the invention has an empirical composition in the as-synthesized form on an anhydrous basis expressed by the empirical formula:

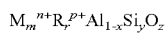

$$M_m^{n+}R_r^{p+}Al_{1-x}Si_yO_z$$

where M is at least one exchangeable cation and is selected from the group consisting of alkali and alkaline earth metals including but not limited to lithium, sodium, potassium, rubidium, cesium, calcium, strontium, barium and mixtures thereof. R is at least one organic cation selected from the group consisting of protonated amines, protonated diamines, quaternary ammonium ions, diquaternary ammonium ions, protonated alkanolamines, and quaternized alkanolammonium ions. Relating the components, "m" is the mole ratio of M to Al and varies from about 0.05 to about 0.95 "r" is the mole ratio of R to Al and has a value of about 0.05 to about 0.95, "n" is the weighted average valence of M and has a value of about 1 to about 2, "p" is the weighted average valence of R and has a value of about 1 to about 2, "y" is the mole ratio of Si to Al and varies from about 3 to about 50 and "z" is the mole ratio of O to Al and has a value determined by the equation:

$$z = (m \cdot n + r \cdot p + 3 + 4 \cdot y)/2$$

The UZM-14 aggregate material of the invention is prepared by a hydrothermal crystallization of a reaction mixture prepared by combining reactive sources of M, R, aluminum and silicon. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates, HiSil and Ultrasil. Sources of the M metals include the halide salts, nitrate salts, acetate salts, and hydroxides of the respective alkali or alkaline earth metals. When R is a quaternary ammonium cation or a quaternized alkanolammonium cation, the sources include the hydroxide, chloride, bromide, iodide and fluoride compounds. Specific examples include without limitation tetraethylammonium hydroxide, tetraethylammonium bromide, diethyldimethylammonium hydroxide and the like. R may also be introduced as an amine, diamine, or alkanolamine such as N,N,N',N'-tetramethyl-1,6-hexanediamine, triethylamine, and triethanolamine.

The reaction mixture containing reactive sources of the desired components, optionally comprising UZM-14 seed, is reacted at a temperature of about 85° C. to about 225° C. and preferably from about 110° C. to about 170° C. for a period of about 1 day to about 2 weeks and preferably for a time of about 2 days to about 6 days in a sealed reaction vessel under autogenous pressure. Effective mixing at between about 100 and about 1000, and preferably about 200 to about 500, revolutions per minute is important for realization of the invention. After crystallization is complete, the solid product is isolated from the heterogeneous mixture by means such as filtration or centrifugation, and then washed with deionized water and dried in air at ambient temperature up to about 100° C.

As synthesized, the UZM-14 will contain some of the exchangeable or charge balancing cations in its channels. These exchangeable cations can be exchanged for other cations, or in the case of organic cations, they can be removed by heating under controlled conditions. Because mordenite is a large-pore zeolite, it is also possible to remove some organic cations directly by ion exchange, for example by aqueous ammoniacal treatment at a pH of from about 10 to about 12.

The catalyst of the invention comprises a refractory inorganic-oxide binder and a metal component. The catalyst also preferably has been subjected to a presulfiding step to incorporate from about 0.05 to about 2 wt.-% sulfur on an elemental basis.

The inorganic-oxide binder component of the invention comprises such materials as alumina, silica, zirconia, titania, thoria, boria, magnesia, chromia, stannic oxide, and the like as well as combinations and composites thereof, for example alumina-silica, alumina-zirconia, alumina-titania, aluminum phosphate, and the like. The binder preferably is selected from one or more of alumina, silica and silica-alumina. Alumina is an especially preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred. An alternative preferred binder is aluminum phosphate as described in U.S. Pat. No. 4,629,717 which is incorporated herein by reference.

The binder and zeolite may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. A preferred method comprises comingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

The catalyst of the invention optionally may comprise an additional zeolitic component, The additional zeolite component preferably is selected from one or more of MFI, MEL, EUO, FER, MFS, MOR, MTT, MTW, MWW, MAZ, TON and FAU (IUPAC Commission on Zeolite Nomenclature) and UZM-8 (see WO 2005/113439, incorporated herein by reference thereto). More preferably, particularly when the catalyst is used in a transalkylation process, the additional zeolitic component consists essentially of MFI. Suitable total zeolite amounts in the catalyst range from about 1 to about 100 wt-%, preferably from about 10 to about 95 wt-%, and more preferably between about 60 and about 90 wt-%.

The catalyst preferably comprises a metal component comprising one or more elements selected from groups VIB(6), VIIB(7), VIII(8-10), IB(11), IIB(12), IIIA(13) and IVA(14) of the Periodic Table. Preferably the metal component is selected from one or more of rhenium, nickel, cobalt, molybdenum and tungsten when the catalyst is used in a transalkylation process. The catalyst also may contain phosphorus. Suitable metal amounts in the transalkylation catalyst range from about 0.01 to about 15 wt-% on an elemental basis, with the range from about 0.1 to about 12 wt-% being preferred, and the range from about 0.1 to about 10 wt-% being highly preferred. The catalyst also preferably has been subjected to a presulfiding step to incorporate from about 0.05 to about 2 wt.-% sulfur on an elemental basis. This presulfiding step may take place either during the manufacture of the catalyst or after the catalyst has been loaded into a process unit.

The finished composite is preferably calcined in an air atmosphere at a temperature of from about 425° to about 750° C., preferably at a temperature of from about 475° to about 550° C., over a period of from about 0.5 to about 10 hours.

The access of reactants to the 12-ring channels of the UZM-14 has been found to be the most important parameter affecting the activity and stability of the catalyst for transalkylation of aromatic hydrocarbons. This access has been found to relate to the size of the crystallites, to mesopore volume and to 12-ring channel openings per unit of zeolite. The most important parameter apparently is crystallite length parallel to the direction of the 12-ring channels, which should be to about 60 nm or less and preferably about 50 nm or less.

EXAMPLES

The following examples are based on test results and characteristics measured on ammonium-exchanged and calcined UZM-14. The appended claims embrace UZM-14 in any stage of manufacture or formulation including as-synthesized or before or after ion exchange and/or before or after calcination. The examples are presented as illustration of the invention and should not be construed as a limitation on the generally broad scope of the invention as set out in the appended claims.

Two samples of UZM-14 were prepared and designated as UZM-14A and UZM-14B in Example 1 for formulation of catalysts and detailed testing. The samples were prepared from NaOH, sodium aluminate, SiO2 (Ultrasil) and tetraethylammonium bromide (TEABr) along with sufficient deionized water, and the crystallization was effected at the indicated temperature with agitation as indicated in revolutions per minute (RPM) over the indicated period of time. The resulting globular aggregates of crystallites were washed three times with deionized water and dried at a temperature of 100° C.

Example 1

|  | UZM-14-A | UZM-14-B |
|---|---|---|
| NaOH (g) | 625 | 625 |
| Na Aluminate (g) | 450 | 451 |
| SiO₂ (Ultrasil) (g) | 3212 | 3241 |
| TEABr (g) | 506 | 506 |
| H₂O (g) | 16,850 | 16,975 |
| Temperature (° C.) | 150 | 150 |
| Mixing (RPM) | 200 | 300 |
| Time (hr) | 66 | 76 |

Samples of known state-of-the-art mordenites were acquired from Zeolyst International and Tosoh Corporation for comparison with the UZM-14 samples. Characteristics of the two UZM-14 samples and the Zeolyst and Tosoh samples are compared in Example 2.

The mean crystallite length parallel to the direction of the 12-ring channels was measured by applying the Scherrer equation to x-ray diffraction data. Prior to analysis, each of the UZM-14 and the commercial mordenites were converted to the hydrogen form by heating the NH4-exchanged form to 540° C. for 2 hours in nitrogen and then for 5 hours in air. Specifically, the full width at half maximum (FWHM) was measured for the (002) diffraction peak of the MOR component at about 23.8° 2θ for CuKα radiation and then the mean crystallite length, L002, parallel to the direction of the 12-ring channels was calculated from the Scherrer equation, $$L_{002} = 0.9 * \lambda / (\beta * \cos(\theta))$$

where λ is the wavelength for CuKα radiation, θ is one-half the diffraction angle, and β is the FWHM for the peak corrected for instrumental broadening, using the equation $$\beta^{1/2} = B^{1/2} - b^{1/2}$$

where B is the measured FWHM for the peak and b is the measured FWHM for an instrumental standard showing only instrumental broadening. It is assumed that the peaks are partially Gaussian and partially Cauchy in shape.

The number of 12-ring channel-openings per gram of MOR framework type zeolite, $N_p$, is inversely proportional to the mean crystallite length parallel to the direction of the 12-ring channels and was estimated from the equation $$N_p = (4 * N^o * c) / (L_{002} * MW)$$

where $N^o$ is Avagadros number ($6.023 * 10^{23}$), c is the c-axis unit cell length, $L_{002}$, is the mean crystallite length parallel to the direction of the 12-ring channels, and MW is the molecular weight of the unit cell contents. For the present samples, this equation reduces to (with $L_{002}$ measured in nm)

$$N_p = 6.2 \times 10^{20} / L_{002}$$

Particle sizes for the UZM-14 samples and for the commercial mordenites were estimated from high resolution SEM images. SEM particle sizes are in general larger than crystallite sizes since the particles can comprise multiple crystallites.

The mesopore volumes for each of these materials were determined from nitrogen sorption isotherms as follows. Prior to analysis, each of the UZM-14 and the commercial mordenites were converted to the hydrogen form by heating the NH4-exchanged form to 540° C. for 2 hours in nitrogen and then for 5 hours in air. The sorption isotherms were then measured and the total pore volume was determined from the nitrogen uptake at the highest value of P/P0 (~0.98). The micropore volume was estimated using the t-plot. The mesopore volume was obtained by subtracting the micropore volume from the total pore volume.

For further testing, each of the UZM-14 powders and the commercial mordenite powders described above were formed into catalysts which contained 0.15% Re, 25% Al2O3 binder and 75% of the UZM-14 or commercial mordenite material. In a typical catalyst preparation, about 100 grams of ammonium exchanged zeolite was extruded with peptized Catapal B alumina to make a 75% zeolite/25% alumina formulation. The extrudates were calcined at 550° C. for 3 hours in air, then rotary impregnated with an aqueous HReO4 solution to target 0.15% Re on the catalyst. The Re containing extrudates were then calcined at 540° C. for 2 hours in air.

An activity test was carried out for each of these catalyst samples in an aromatics transalkylation test. The overall conversion, a weighed average of the transalkylation, dealkylation and disproportionation reactions, was measured at 350° C. at a reactor pressure=250 psig, a weight hourly space velocity=4 and a H2:HC ratio=6. The catalysts were sulfided in the test unit by doping the feed with excess dimethyl disulfide (250 ppm S) for the first hour of the test. The S/Re molar ratio on the spent catalysts is typically in the 0.5-0.8 range. The feed had nominally the following composition in weight percent:

| | |
|---|---|
| Toluene | 75 |
| Propylbenzene | 2 |
| Methylethylbenzene | 10 |
| Trimethylbenzene | 9.7 |
| Indane | 0.8 |
| Methylpropylbenzene | 1.0 |
| Diethylbenzene | 0.4 |
| Dimethylethylbenzene | 1.0 |
| $C_{11}+$ aromatics | 0.1 |

Comparative conversion results for the transalkylation of the aforementioned feed for each of these catalysts as well as characteristics of the Zeolyst and Tosoh samples are shown in Example 2.

Example 2

| | UZM-14-A | UZM-14-B | Zeolyst CBV 21A | Tosoh HSZ-643NHA |
|---|---|---|---|---|
| $L_{002}$ (nm) | 47 | 50 | 68 | 78 |
| Number of 12-ring channel-openings per gram of zeolite | $1.4 \times 10^{19}$ | $1.3 \times 10^{19}$ | $0.91 \times 10^{19}$ | $0.79 \times 10^{19}$ |
| Mean particle size, nm | 106 | 81 | 167 | 170 |
| Maximum particle size, nm | 207 | 186 | 617 | 430 |
| 90% < (nm) | 175 | 143 | 273 | 299 |
| 80% < (nm) | 144 | 110 | 233 | 244 |
| 70% < (nm) | 129 | 99 | 209 | 198 |
| Mesopore Volume (cc/g) | 0.13 | 0.22 | 0.08 | 0.06 |
| Activity Test, % Conversion at 350° C. | 32.8 | 36.8 | 26.5 | 25.7 |

Example 3

Additional UZM-14 samples were prepared in similar manner of UZM-14A and UZM-14B with slight variations to the parameters discussed in Example 1, and the crystallite length parallel to the direction of the 12-ring channels, the mesopore volume, and the conversion were determined for each of the samples:

| Material | $L_{002}$ (nm) | Mesopore Volume (cc/g) | % Conversion at 350° C. |
|---|---|---|---|
| UZM-14-A | 46.6 | 0.13 | 32.8 |
| UZM14-B | 50.4 | 0.22 | 36.8 |
| UZM-14-C | 43.9 | 0.14 | 33.8 |
| UZM-14-D | 45.0 | 0.32 | 39.5 |
| UZM-14-E | 44.2 | 0.35 | 38.8 |
| UZM-14-F | 40.8 | 0.15 | 35.9 |
| UZM-14-G | 42.0 | 0.38 | 43.6 |
| UZM-14-H | 41.3 | 0.27 | 41.8 |
| UZM-14-I | 43.9 | 0.14 | 34.4 |
| UZM-14-J | 42.2 | 0.29 | 40.0 |
| UZM-14-K | 40.6 | 0.32 | 40.3 |
| UZM-14-L | 43.4 | 0.20 | 38.7 |
| Zeolyst | 68.2 | 0.08 | 26.5 |
| Tosoh | 77.9 | 0.06 | 25.7 |

The above results are shown in the attached three-dimensional FIGURE, with the vertical line below each point representing % conversion above the base of 25%. The above results clearly show the advantage of lower crystallite length parallel to the direction of the 12-ring channels and also of increased mesopore volume.

Example 4

The UZM-14-A and UZM-14-B materials described above were formed into catalysts by blending a mixture of 50% UZM-14, 25% MFI zeolite and 25% to peptized Catapal B with a solution of nickel nitrate, ammonium heptamolybdate and phosphoric acid, to obtain catalysts with 0.45% Ni, 2% Mo and 0.3% P. After extrusion, the catalysts were calcined at 500° C. for 2 hours in air.

These catalysts were then tested for activity under identical conditions as used in Example 9, with the exception that the sulfiding phase was extended to 20 hours to allow enough time for complete sulfiding of the larger amount of metals. The resulting conversions at 350° C. were as follows:
UZM-14-A 39.7%.
UZM-14-B 44.5%.

Example 5

For further testing, UZM-14 powder and a commercial mordenite powder from Zeolyst, CBV 21A, each were formed in a similar manner into catalysts which contained 0.15% Re, 25% Al2O3 binder and 75% of the UZM-14 or commercial mordenite material. Ammonium exchanged zeolite was extruded with peptized Catapal B alumina to make a 75% zeolite/25% alumina formulation. The extrudates were calcined at 550° C. for 3 hours in air, then rotary impregnated with an aqueous $HReO_4$ solution to target 0.15% Re on the catalyst. The Re containing extrudates were then calcined at 540° C. for 2 hours in air.

Pilot-plant tests were carried out on each of the catalysts at a pressure of 400 psig, weight hourly space velocity of 4, H2//HC ratio of 4 and temperature as required to maintain 50% conversion. The test was run at these conditions to a catalyst life of 2.8 barrels of hydrocarbon feed/pound of catalyst The catalysts were sulfided in the test unit prior to testing for 6 hours at 4 WHSV and H2/HC of 4 in a hydrocarbon feed that contained 10 ppm sulfur as dimethyl disulfide (DMDS) at 280° C. and 400 psig. The feed had nominally the following composition in weight percent:

| | |
|---|---|
| Toluene | 50 |
| C9 aromatics | 37 |
| C10 aromatics | 12 |
| $C_{11}+$ aromatics | 1 |

The Table below displays the results of this test. The UZM-14 based catalyst showed an activity advantage of about 20° C. A small advantage in catalyst stability (lower rate of temperature increase to maintain stable conversion) is also shown. These two features would couple together to lead to a longer run length for this catalyst before it would need to be replaced or regenerated. Importantly, the UZM-14 based catalyst also shows improved levels of the most desired product xylene in the reactor effluent.

Example 5

Test Results

| | Zeolyst CBV 21A Based Catalyst | UZM-14 Based Catalyst |
|---|---|---|
| Temperature to reach 50% conversion after 1 BPP* | 387° C. | 367° C. |
| Rate of Temperature Increase Required to maintain 50% conversion between 1 and 2.8 BPP (° C./BPP) | 2.1 | 1.8 |
| % Xylene in Reactor Product (H2-free) | 28.9% | 29.4% |

BPP = Barrels of HCBN feed/Lb. Catalyst

Example 6

Further comparative tests of UZM-14 and the commercial Zeolyst mordenite were carried out. The UZM-14-A and Zeolyst CBV 21A mordenite powders were separately formed into catalysts by blending a mixture of 50% UZM-14 or Zeolyst CBV 21A mordenite powder, 25% MFI zeolite and 25% peptized Catapal B with a solution of ammonium heptamolybdate to obtain catalysts containing 3% Mo. After extrusion, the catalysts were calcined for 2 hours in air.

Pilot-plant tests were carried out on each of the catalysts at a pressure of 400 psig, weight hourly space velocity of 3, H2//HC ratio of 3 and temperature as required to maintain 50% conversion. The catalysts were sulfided in the test unit prior to testing for 18 hours at 3 WHSV and H2/HC of 3 in a hydrocarbon feed that contained 250 ppm sulfur as dimethyl disulfide (DMDS) at temperatures between 280 and 360° C. and 400 psig. The feed had nominally the following composition in weight percent:

| | |
|---|---|
| Toluene | 50 |
| $C_9$ aromatics | 38 |
| C10 aromatics | 8 |
| C11+ aromatics | 4 |

The Table below displays the results of this test. The UZM-14 based catalyst showed an activity advantage of about 19° C. A significant advantage in catalyst stability (lower rate of temperature increase to maintain stable conversion) is also shown. These two features would couple together to lead to a longer run length for this catalyst before it would need to be replaced or regenerated. Importantly, the UZM-14 based catalyst also shows significantly improved levels of the most desired product xylene in the reactor effluent.

Example 6

Test Results

| | Zeolyst CBV 21A Based Catalyst | UZM-14 Based Catalyst |
|---|---|---|
| Temperature to reach 50% conversion after 1 BPP* | 386° C. | 367° C. |
| Rate of Temperature Increase Required to maintain 50% conversion between 1 and 2.8 BPP (° C./BPP) | 4.9 | 3.1 |
| % Xylene in Reactor Product (H2-free) | 32.7% | 33.6% |

BPP = Barrels of HCBN feed/Lb. Catalyst

The invention claimed is:

1. A process for transalkylation of a feedstream comprising one or more of $C_7$, $C_9$, $C_{10}$ and $C_{11}+$ aromatics to obtain a product stream having an increased concentration of $C_8$ aromatics relative to that of the feedstream, comprising contacting the feedstream at transalkylation conditions with a catalyst comprising:
    (a) an aggregate material comprising globular aggregates of crystallites having a MOR framework type comprising 12-ring channels, a mesopore volume of at least about 0.10 cc/gram, a mean crystallite length parallel to the direction of the 12-ring channels of about 60 nm or less, the number of 12-ring channel-openings per gram of zeolite of at least $1 \times 10^{19}$ and a silica-alumina $(Si/Al_2)$ mole ratio of from about 8 to about 50;
    (b) a binder selected from one or more of alumina, silica and silica-alumina; and,
    (c) a metal component comprising one or more elements selected from groups VIB(6), VIIB(7), VIII(8-10) and IVA(14) of the Periodic Table.

2. The process of claim 1 wherein the feedstream further comprises benzene.

3. The process of claim 1 wherein the feedstream further comprises $C_8$ aromatics.

4. The process of claim 1 wherein the feedstream further comprises aromatic compounds having from 2 to 4 rings.

5. The process of claim 4 wherein the feedstream further comprises a bottoms stream from the fractionation of $C_8$ aromatics from the transalkylation product stream.

6. The process of claim 1 wherein the transalkylation conditions comprise a temperature from about 200° C. to about 540° C., a pressure from about 100 kPa to about 6 MPa absolute, and a space velocity from about 0.1 to about 20 hr$^{-1}$.

7. A process for transalkylation of a feedstream comprising one or more of $C_7$, $C_9$, $C_{10}$ and $C_{11}+$ aromatics to obtain a product stream having an increased concentration of $C_8$ aromatics relative to that of the feedstream, comprising contacting the feedstream at transalkylation conditions with a catalyst suitable for the conversion of aromatic hydrocarbons comprising:
    (a) an aggregate material comprising globular aggregates of crystallites having a MOR framework type comprising 12-ring channels, a mesopore volume of at least about 0.10 cc/gram, a mean crystallite length parallel to the direction of the 12-ring channels of about 60 nm or less, the number of 12-ring channel-openings per ram of zeolite of at least $1 \times 10^{19}$ and a silica-alumina (Si/Al$_2$) mole ratio of from about 8 to about 50;
(b) an additional zeolitic component selected from one or more of MFI, MEL, EUO, FER, MFS, MTT, MTW, TON, MOR and FAU;
(c) a binder comprising one or more of alumina, silica and silica-alumina; and,
(d) a metal component comprising one or more elements selected from groups VIB(6), VIIB(7), VIII(8-10) and IVA(14) of the Periodic Table.

8. The process of claim 7 wherein the feedstream further comprises aromatic compounds having from 2 to 4 rings.

9. The process of claim 8 wherein the feedstream further comprises a bottoms stream from the fractionation of C$_8$ aromatics from the transalkylation product stream.

10. The process of claim 7 wherein the transalkylation conditions comprise a temperature from about 200° C. to about 540° C., a pressure from about 100 kPa to about 6 MPa absolute, and a space velocity from about 0.1 to about 20 hr$^{-1}$.

11. The process of claim 7 wherein the additional zeolitic component consists essentially of MFI.

\* \* \* \* \*